(12) United States Patent
Farha et al.

(10) Patent No.: US 11,302,449 B2
(45) Date of Patent: Apr. 12, 2022

(54) METHOD AND SYSTEM FOR PATIENT TREATMENT MANAGEMENT USING INTERACTIVE DIGITAL BEST PRACTICE TREATMENT GUIDELINES

(71) Applicant: Avident Health, LLC, Baltimore, MD (US)

(72) Inventors: Maen J. Farha, Baltimore, MD (US); Kamel Jabbour, Richmond (GB)

(73) Assignee: AVIDENT HEALTH, LLC, Baltimore, MD (US)

( * ) Notice: Subject to any disclaimer, the term of this patent is extended or adjusted under 35 U.S.C. 154(b) by 935 days.

(21) Appl. No.: 14/640,975

(22) Filed: Mar. 6, 2015

(65) Prior Publication Data

US 2016/0012189 A1 Jan. 14, 2016

Related U.S. Application Data

(60) Provisional application No. 62/055,383, filed on Sep. 25, 2014, provisional application No. 62/022,860, filed on Jul. 10, 2014.

(51) Int. Cl.
G16H 70/20 (2018.01)
(52) U.S. Cl.
CPC .................. *G16H 70/20* (2018.01)
(58) Field of Classification Search
CPC ...... G06F 19/325; G06F 19/328; G06F 19/00; G06F 19/327; G06F 19/3437; G06F 19/322; G06F 19/345; G06F 19/3481; G06F 3/0482; G06F 3/04842; G06Q 10/0631; G06Q 10/06; G06Q 50/24; G16H 70/20; G16H 10/60; G16H 50/20; G16H 40/20; G16H 50/50; G16H 50/70
See application file for complete search history.

(56) References Cited

U.S. PATENT DOCUMENTS

| | | | |
|---|---|---|---|
| 9,582,838 B1 * | 2/2017 | Henderson | ............. G16H 40/63 |
| 2003/0110059 A1 * | 6/2003 | Janas, III | ............. G06F 19/325 |
| | | | 705/2 |
| 2006/0031094 A1 * | 2/2006 | Cohen | ................... G16H 20/10 |
| | | | 705/2 |

(Continued)

*Primary Examiner* — Gregory D. Moseley
(74) *Attorney, Agent, or Firm* — Wilson Sonsini Goodrich & Rosati

(57) ABSTRACT

A process that facilitates patient treatment management by allowing users to adhere to guidelines, best practices and medical procedures. For each individual patient the process software automatically recommends individualized treatment plans, medical tests that should be carried out, deviations or exceptions to recommended treatments and medical or clinical trials that the patient may be eligible to take part in. The process software will monitor and display in real time all patients being treated by a physician or at a hospital, surgery, clinic or other institution and display at what stage, test, specialty or procedure, or treatment each patient is currently located along a particular guideline, best practice or medical procedure and the cost included either at each stage or so far in the treatment path. The process software will also monitor and display for individual patient and in a consolidated manner financial, user and administrative information in real time.

18 Claims, 27 Drawing Sheets

(56) References Cited

U.S. PATENT DOCUMENTS

| | | | | |
|---|---|---|---|---|
| 2006/0235280 | A1* | 10/2006 | Vonk | G06F 19/3481 600/300 |
| 2008/0281639 | A1* | 11/2008 | Quinn | G06Q 10/10 705/3 |
| 2009/0119282 | A1* | 5/2009 | Load | G06F 19/325 |
| 2011/0208540 | A1* | 8/2011 | Lord | G06F 19/325 705/2 |
| 2011/0301977 | A1* | 12/2011 | Belcher | G06F 19/345 705/3 |
| 2012/0066000 | A1* | 3/2012 | Opfer | G06F 19/325 705/3 |
| 2012/0101847 | A1* | 4/2012 | Johnson | G06Q 30/00 705/3 |
| 2012/0231959 | A1* | 9/2012 | Elton | G06Q 50/22 506/2 |
| 2013/0166317 | A1* | 6/2013 | Beardall | G06F 19/322 705/2 |
| 2013/0226617 | A1* | 8/2013 | Mok | G06F 19/322 705/3 |
| 2013/0317844 | A1* | 11/2013 | Hammond | G06Q 50/22 705/2 |
| 2014/0058742 | A1* | 2/2014 | Chari | G16H 50/20 705/2 |
| 2014/0108024 | A1* | 4/2014 | Evans | G06Q 50/24 705/2 |
| 2014/0249851 | A1* | 9/2014 | Christodouleas | G06F 19/325 705/3 |
| 2014/0316821 | A1* | 10/2014 | Sheffield | G16B 50/00 705/3 |

\* cited by examiner

Fig. 3

VIEW FULL HISTORY

Find:

Date: dd / mm / yyyy to dd / mm / yyyy  [Search]

| Note | Date | By |
|---|---|---|
| Lorem ipsum dolor sit amet, consectetur adipiscing elit. Aliquam tristique... | 22/12/2010 14:45 | Jones |
| Bibendum neque a vestibulum. Pellentesque porttitor erat eu lorem. | 30/12/2009 07:44 | Williams |
| Posuere et posuere turpis varius. Donec adipiscing porttitor scelerisque... | 19/08/2010 15:42 | Davies |
| Praesent non augue est. Nunc quis arcu est. Praesent sit amet odio et... | 19/08/2010 15:42 | Evans |
| Augue porttitor mattis. Cras imperdiet, risus non varius sollicitudin, arcu... | 27/05/2010 11:52 | Roberts |
| Purus ultricies nisi, nec tempus orci lorem non tortor. Mauris id dui... | 30/04/2010 14:56 | Morgan |
| Nullam at euismod purus. Donec in arcu justo. | 27/06/2010 11:31 | Edwards |
| Bibendum arcu, sit amet convallis odio eleifend sit amet... | 04/08/2010 06:49 | Smith |
| Sed et ligula at lorem sodales lacinia ut quis metus. Mauris cursus sodales... | 08/03/2010 18:54 | Phillips |
| Lorem ipsum dolor sit amet, consectetur adipiscing elit. Aliquam tristique... | 02/10/2009 09:04 | Richards |

Fig. 7

PATIENTS

Find: [      ] [Search]

| Patient name | Lead consultant | Date of Birth | Gender | Insurance number | SSN | Hospital ref. number | Edit | Archive |
|---|---|---|---|---|---|---|---|---|
| Sofia B. Jones | Oliver Jones | 14/08/2011 | Male | | 77 992547 357199 9 | 86155 | | |
| Jenny Doh | Daniel Williams | 20/03/2010 | Female | 04353 | 41 109725 029285 2 | 04353 | | |
| Emily Salo | Thomas Davies | 11/12/2007 | Male | 41606 | 96 914524 102803 1 | 41606 | | |
| Karl Walton | Harry Evans | 07/09/2008 | Female | | 78 697451 985003 0 | 47761 | | |
| Giovanna G. Izguierdo | Jack Roberts | 18/11/2009 | Male | 87682 | 18 723777 675732 4 | 87682 | | |
| Emma Anderson | Samuel Morgan | 08/08/2003 | Female | 46547 | 59 987387 133844 6 | 46547 | | |
| Samantha Kirkland | James Edwards | 05/12/2010 | Male | | 55 468356 086995 3 | 69844 | | |
| Madison Kenney | Alexander Smith | 09/04/2005 | Female | 08535 | 77 992547 357199 9 | 08535 | | |
| Jane Smith | Charlie Phillips | 14/07/2007 | Male | 60842 | 41 109725 029285 2 | 60842 | | |
| Harry Lee | Emma Richards | 05/10/2006 | Female | 06844 | 96 914524 102803 1 | 06844 | | |

JOHN SMITH

Contact details    phone/address/...    Lead consultant    Dr Oliver Wood    View full history Other consultants    Dr Smith, Dr Brown

| Vital signs record | Diagnosis | Test results | Treatment progress 0 | Treatment progress 1 | Treatment progress 2 |

TEST RESULTS

| Test | Result | Date | History | Edit |
|---|---|---|---|---|
| ER | Pos | 22/12/2010 14:45 | 4 other tests | ✎ |
| PR | Pos | 30/12/2009 07:44 | 1 other test | ✎ |
| HER2 | Neg | 19/08/2010 15:42 | No other test | ✎ |
| CBC | 100 | 19/08/2010 15:42 | 5 other tests | ✎ |
| Platelets | 1000 | 27/05/2010 11:52 | 4 other tests | ✎ |
| Liver function | 4 | 30/04/2010 14:56 | 1 other test | ✎ |
| Alkaline phosphatase | 12 | 27/06/2010 11:31 | No other test | ✎ |
| Bone scan | Normal | 04/08/2010 06:49 | 8 other tests | ✎ |
| Chest imaging | Abnormal | 01/03/2010 18:54 | 4 other tests | ✎ |
| ER | Pos | 02/10/2009 09:04 | 1 other test | ✎ |

Fig. 13

LICENSE TYPES

| Name | Trial period | Cost (per patients per month) | Maximum number of patients | Edit | Delete |
|---|---|---|---|---|---|
| Hospitals | 1 month | €15.20 | 50 | ✎ | ✗ |
| Healthcare systems | 3 months | €37.80 | 200 | ✎ | ✗ |
| Independent physicians | 6 months | €81.00 | 500 | ✎ | ✗ |
| Physician groups | 1 month | €15.00 | 1000 | ✎ | ✗ |

Add new

Fig. 14

JOHN SMITH

Contact details | phone/address/... | Lead consultant | Dr Oliver Wood | Warning about license

[ Audit trail | Other consultants | Nurses ]

AUDIT TRAIL

Find: [_____]
Show: [ -- All -- ▼ ]  [Search]

| Action | Date and time | By |
|---|---|---|
| Patient registered in the system | 22/12/2010 14:45 | John Smith (Admin) |
| Address changed from XYZ1 to XYZ2 | 30/12/2009 07:44 | John Smith (Admin) |
| SSN change to from 00000 to 123123123 | 19/08/2010 15:42 | Jackie Brown (Nurse) |
| Treatment A | 19/08/2010 15:42 | Oliver Wood (Lead) |
| Treatment B | 27/06/2010 11:52 | John Smith (Admin) |
| Lead consultant changed from Dr. A to Dr. B | 30/04/2010 14:56 | John Smith (Admin) |

Submitted changes

CHANGES

| Pathway | Date | State | Notes | View | Reject | Confirm |
|---|---|---|---|---|---|---|
| Breast Cancer | 14/06/2011 | Waiting for review | | View | Reject | Confirm |
| Breast Cancer | 20/03/2010 | Waiting for review | | View | Reject | Confirm |
| Breast Cancer | 11/12/2007 | Accepted | | View | Reject | Confirm |
| Breast Cancer | 07/09/2008 | Rejected | Praesent non augue est. Nunc quis arcu est. Praesent sit amet odio et... | View | Reject | Confirm |

Fig. 18

PATIENTS

Find: [----Select----▼]
Customer: [Search]

| Customer | Patient First name | Patient Last name | Date of Birth | Gender | Insurance number | SSN | Hospital ref number | Move to another customer |
|---|---|---|---|---|---|---|---|---|
| Johns Hopkins | Oliver | Jones | 14/06/2011 | Male | | 77 992547 357199 9 | 86193 | Move |
| Cedars Sinai | Daniel | Williams | 20/03/2010 | Female | 04353 | 41 109725 029385 2 | 04353 | Move |
| Cleveland Clinic | Thomas | Davies | 11/12/2007 | Male | 41606 | 96 944524 832803 1 | 41606 | Move |
| New York University Hospital | Harry | Evans | 07/09/2008 | Female | | 78 697451 988031 0 | 47763 | Move |
| George Washington General Hospital | Jack | Roberts | 18/11/2009 | Male | 87682 | 18 783777 675732 4 | 87682 | Move |
| Johns Hopkins | Samuel | Morgan | 08/08/2001 | Female | 46547 | 59 987387 033846 6 | 46547 | Move |

Fig. 21

JOHN SMITH

Contact details: phone/address/...
Other consultants: Dr Smyth, Dr Brown
Local consultant: Dr Oliver Wood View full history

| Vital signs record | Diagnosis | Test results | Treatment progress 0 | Treatment progress 1 | Treatment progress 2 |

VITAL SIGNS RECORD

| Visit date | BP | HR | Height | Weight | Edit |
|---|---|---|---|---|---|
| 14/06/2011 | 100/80 | 80 | 120 | 95 | ✎ |
| 20/03/2010 | 102/85 | 91 | 120 | 95 | ✎ |
| 11/12/2007 | 120/76 | 72 | 120 | 95 | ✎ |
| 07/09/2008 | 100/80 | 85 | 120 | 95 | ✎ |
| 18/11/2009 | 102/85 | 76 | 120 | 95 | ✎ |
| 08/08/2001 | 120/76 | 80 | 120 | 95 | ✎ |
| 25/12/2010 | 100/80 | 91 | 120 | 95 | ✎ |
| 09/04/2005 | 102/85 | 72 | 120 | 95 | ✎ |

Fig. 22

OUTGOING AND SENT EMAILS

| Customer | To | Subject | View text | Date sent | Error |
|---|---|---|---|---|---|
| Johns Hopkins | jim@fakemail.com | subject 1 | View text | 14/06/2011 | |
| Cedars Sinai | jack@office.edu | subject 2 | View text | 20/03/2010 | |
| Cleveland Clinic | alice2001@uat.co | subject 3 | View text | 11/12/2007 | |
| New York University Hospital | ted.smith@williams.com | subject 4 | View text | 07/09/2008 | |
| George Washington General Hospital | albert@for-test.net | subject 5 | View text | 18/11/2009 | Invalid email |
| Johns Hopkins | janderson@college.edu | subject 6 | View text | 08/08/2001 | |
| Cedars Sinai | Robert_jackson@humour.org | subject 7 | View text | 25/12/2010 | |
| Cleveland Clinic | jim@fakemail.com | subject 8 | View text | 09/04/2005 | |
| New York University Hospital | jack@office.edu | subject 9 | View text | 14/07/2007 | |
| George Washington General Hospital | alice2001@uat.co | subject 10 | View text | 05/10/2006 | |

Send mass email

JOHN SMITH

Contact details phone/address/...

Lead consultant     Dr Oliver Wood

Audit trail | Other consultants | Nurses

NURSES

| Name | Is currently assigned |
|---|---|
| Oliver Jones | |
| Daniel Williams | |
| Thomas Davies | ✓ |
| Harry Evans | |
| Jack Roberts | ✓ |
| Samuel Morgan | |
| James Edwards | ✓ |
| Alexander Smith | |
| Charlie Phillips | ✓ |
| Emma Richards | |

Fig. 25

CHANGES

| Pathway | Date | State | Notes | Action |
|---|---|---|---|---|
| Breast Cancer | 14/06/2011 | In progress | | Cancel |
| Breast Cancer | 20/03/2010 | Waiting for review | | Cancel |
| Breast Cancer | 11/12/2007 | Accepted | | Submit |
| Breast Cancer | 07/09/2008 | Rejected | | Confirm |
| Breast Cancer | 18/11/2009 | In progress | | Cancel |
| Breast Cancer | 08/08/2001 | Waiting for review | | Submit |
| Heart Disease | 25/12/2010 | Accepted | | Cancel |
| Heart Disease | 09/04/2005 | Rejected | | Cancel |
| Lung Cancer | 14/07/2007 | In progress | | Submit |
| Breast Cancer | 05/10/2006 | Waiting for review | Lorem ipsum dolor sit amet, consectetur adipiscing elit. Aliquam tristique... | Confirm |

Change in progress (02/02/2014) Submit

Fig. 27

METHOD AND SYSTEM FOR PATIENT TREATMENT MANAGEMENT USING INTERACTIVE DIGITAL BEST PRACTICE TREATMENT GUIDELINES

CROSS-REFERENCE

This application claims priority from U.S. Provisional Patent Application Ser. No. 62/022,860 which was filed on Jul. 10, 2014, and U.S. Provisional Patent Application Ser. No. 62/055,383 which was filed on Sep. 25, 2014, the entire contents of which are expressly incorporated by reference herein.

BACKGROUND OF THE INVENTION

The present invention relates to the field of medical treatments and, more specifically, to predicting treatment efficacy and determining optimal treatment for any illness, disease or abnormality. This invention also relates to interactive methods for delivering information to a healthcare provider which motivates him to take action and facilitates such action which will improve a healthcare consumer's compliance with desired best practice health care protocols.

Healthcare providers spend significant amounts of time outside of seeing their patients to learn how to use new tools, and reviewing relevant cases to their practice in assessing, diagnosing, planning, and/or preparing for performing a treatment for their patients. However, once in the surgical or diagnostic suite, or other facility or location where the treatment is to be performed, the health care provider is largely left to relying on his or her own memory to effectively use the many tools at his or her disposal during the treatment. The health care provider may often encounter unexpected developments or complications during the treatment that may not have been anticipated prior to beginning the treatment. For example the treatment for breast cancer follows a complex pathway of actions with progress to the next treatment based on multiple factors and pre-determined trigger points. The latest treatment guideline by the National Comprehensive Cancer Network (NCCN) covers approximately one hundred and twenty nine pages and it is therefore difficult for attending physicians to monitor the treatment of a patient as they progress through the treatment because it is not at all easy to memorize and apply the guidelines in totality. There are electronic/web-based versions of the NCCN guidelines in existence but these tend to be limited to online reference guides and do not automatically map the patient to the required treatment based on the latest clinical diagnosis, test results and previous treatments.

The problem identified above has not been solved to-date in an effective and accurate manner.

The limitations and the non-cost effectiveness of prior art are overcome by the instant invention as described below.

BRIEF SUMMARY OF THE INVENTION

This invention at first creates a searchable, dynamic and rule-based database. This database is at first created with the help of best practice guidelines made available by reliable organizations, mainly government bodies, medical institutions, professional associations or not for profit organizations. The guidelines which are prescribed by the government bodies are there in "PDF" format.

All pathway steps, next steps, rules, clinical conditions and next treatment options are manually entered into a searchable, dynamic and rule-based database. Interaction with the database created originates with from the original diagnosis of the physician. The health care provider enters the specific diagnosis. For example" the health care provider must enter predetermined fields encompassing critical medical information such as type of tumor, size, ER/PR positive, and other key information.

Once the relevant information is entered by the health care provider, the instant invention displays a visual and/or text representation of the previous and next treatment steps for each patient and the location of the patient on the entire pathway or on a specific section of the pathway in a visual manner utilizing flow diagrams or other visual methods or charts.

The health care provider utilizes the information provided to him by the instant invention and decides what step is to be followed for the treatment of the patient. The health care provider is at liberty to follow the suggestions made by the invention or ignore it on the basis of his personal knowledge. The instant invention intelligently records the choices made by the health care provider in order to improve the database continuously. The instant invention may also link directly to third party databases which may help in automatically identifying patients suitable for certain clinical trials based on the diagnosis provided by the healthcare professional.

It is the objective of the instant invention to create a process which can effectively and intelligently help health care providers to utilize the guidelines applicable to any treatment.

These and other features, objects and advantages of the present invention will be readily clear to persons of ordinary skill in the art upon reading the entirety of this disclosure, which includes the accompanying drawings and claims.

BRIEF DESCRIPTION OF THE DRAWINGS

FIG. 3 shows an example of a physician's consolidated patient view.

FIG. 7 shows an example of all changes made to the system.

FIG. 9 shows an example of a secure and confidential database of patient demographics and identifying information.

FIG. 12 shows another example of an individual patient's progress along the relevant pathway.

FIG. 13 shows an example of a view of all tests that have taken place for each individual patient, the result of the test, the time and date of the test.

FIG. 14 shows an example of a view of license tab.

FIG. 16 shows an example of a view of the audit trail to track changes to each patient's record.

FIG. 17 shows an example of user maintenance, access permissions and password details.

FIG. 18 shows an example of an interface to allow for editing the underlying database of guidelines or treatment best practices.

FIG. 21 shows an example of an individual patient details screen.

FIG. 22 shows an example of a display of each visit by a patient.

FIG. 23 shows an example of a view of messages sent to clients by owner or administrator.

FIG. 24 shows an example of a display of patient's insurance details and lead physician attending each patient.

FIG. 25 shows an example of a nurses tab.

FIG. 27 shows another example of an interface to allow for editing the underlying database of guidelines or treatment best practices.

DETAILED DESCRIPTION OF THE INVENTION

In the present disclosure, numerous specific details are provided, such as examples of module, components, and method, to provide a thorough understanding of embodiments of the invention. Persons of ordinary skill in the art will recognize, however, that the invention can be practiced without one or more of the specific details. In other instances, well-known details are not shown.

The first step in the process is to create a dynamic, searchable and rule:based database with the help of guidelines provided by the government or other organizations. The database is created by manually entering the information provided in the guideline. In the instant disclosure NCCN guidelines for the treatment of breast cancer has been taken as an example, though it must be understood that the invention is in no way restricted to the NCCN guideline.

The NCCN guidelines for the treatment of breast cancer which are provided in pdf form are entered into a database manually are entered into the database manually and a rule-based mathematical representation is created to ensure that next treatment options are only recommended when prerequisite conditions have been met. Third party clinical trials database is also created or is linked to publicly available databases directly. The database so created is a searchable so that the relevant patient information can be matched and results can be generated in accordance with the instant invention. In the same manner third party clinical database is also created.

Figure 1:
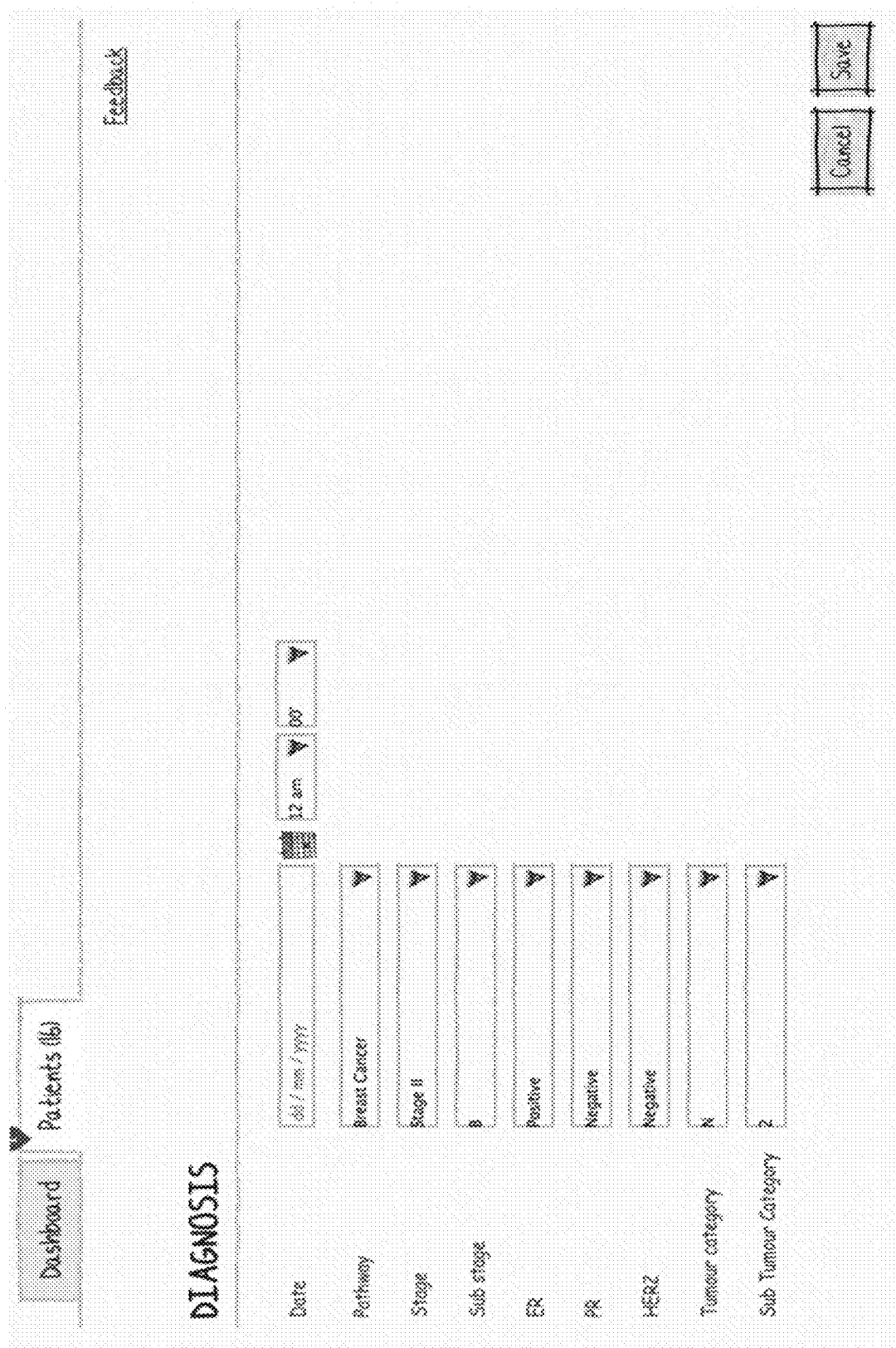
FIG. 1 shows an example of an initial diagnosis screen.

FIG. 1 shows the diagnosis screen whereby specific details on patient condition, tumor size, status and stage are entered. The initial screen the user, typically a physician, will utilize upon primary consultation with a patient. The user mainly a health service provider inputs the medical history, test results and current diagnosis into the system. Underlying this module will be the relevant treatment pathway or guideline, which has been digitized and coded into a dynamic database, which ensures that the diagnosis input fields are able to identify the relevant position on the treatment pathway. A module that allows the user to input patient information, medical history, test results and create a diagnostic workup and treatment plan in addition to displaying an overview of the patient's progress along a treatment plan.

Figure 2:
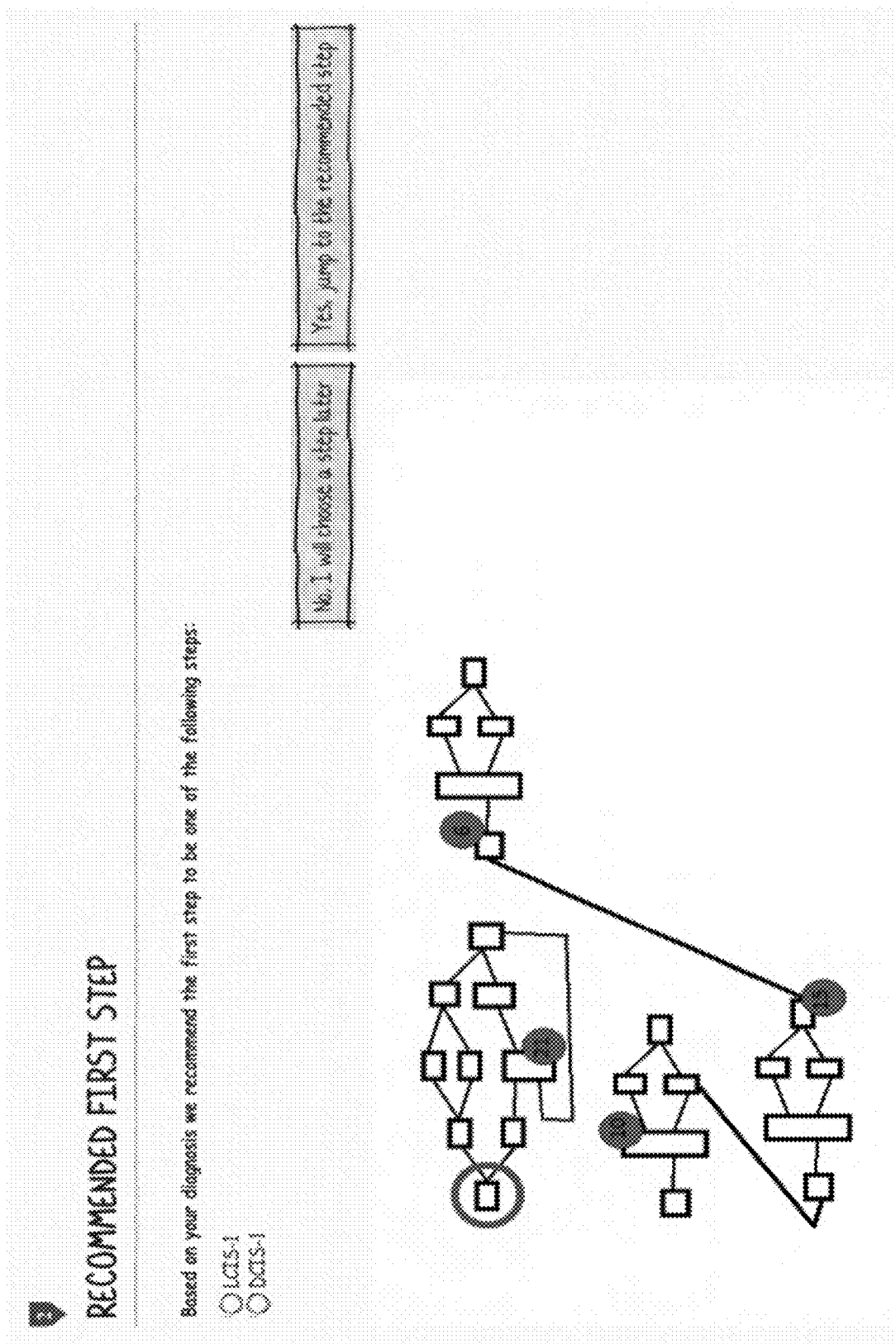
FIG. 2 shows an example of a pathway location screen.

FIG. 2 shows the pathway location screen whereby a patient is placed on the correct coordinates on the treatment pathway. This screen is the output from the detailed clinical diagnosis entered into the process software and allows for the system to overlay the patients current condition onto the correct treatment recommended as specified in a treatment guideline or best practice (for example such as the NCCN guidelines on great cancer treatment or other treatments). The eligibility criteria from relevant clinical trials are entered into the underlying database or linked directly to relevant open source third party clinical trial databases which ensure that should a diagnosis match the required pre-requisite conditions for a relevant clinical trial the user may enter a patient automatically into such medical or clinical trials. This solution ensures that users (such as the supervising physician or other users) can ratify all next treatment step recommendations electronically. A user may choose not to follow the recommended step. However, the system will prompt the user to input justification for any deviation to the recommended treatment. All deviations from the recommended treatment will be recorded and consolidated to allow for further analysis to determine any reasons for deviation trends and whether improvements to the underlying guidelines are required and whether the pathway or treatment guideline owner needs to be informed of any deviations or anomalies. The process software will position the patient at the most relevant point on a treatment pathway based on the patient's current condition, medical history and test results.

Figure 3:
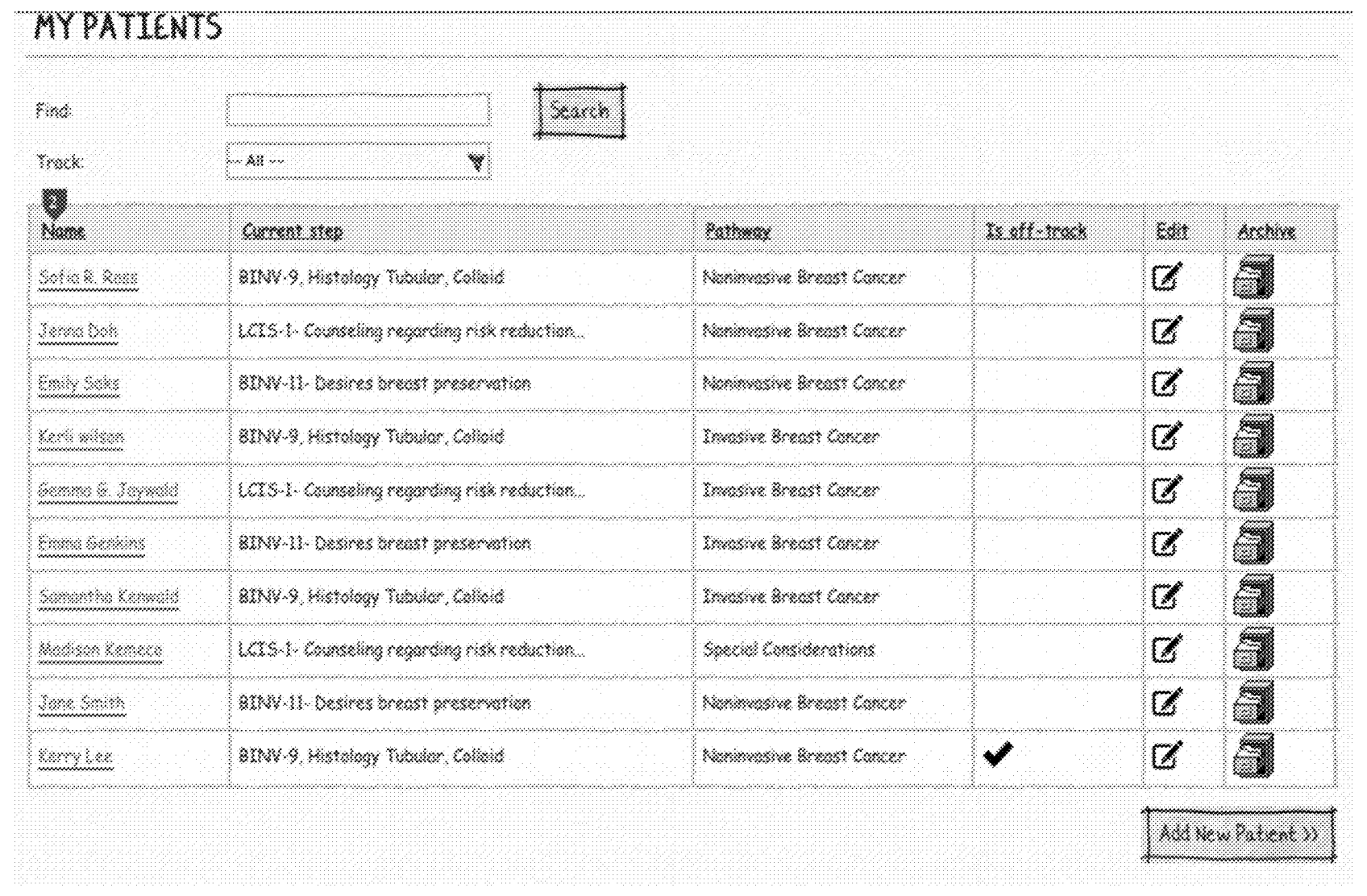

FIG. 3 shows a physician's consolidated patient view. The user can view a detailed record of the treatment history, test results, clinical trial eligibility and possible next treatment options for ratification by the physician for each patient. Maintain a record and create alerts for guideline deviation and noncompliance to treatment best practice or guidelines. This module ensures that the user is automatically informed of all test results and treatment results for each patient. Patients that have recently undergone a procedure or test by a third party specialist or nurse will appear in this section and the supervising physician will have the ability to accept or reject any results for each individual patient. The user can transfer a patient including all details on medical history and test results to another physician or medical institution, hospital or other organization.

Figure 4:
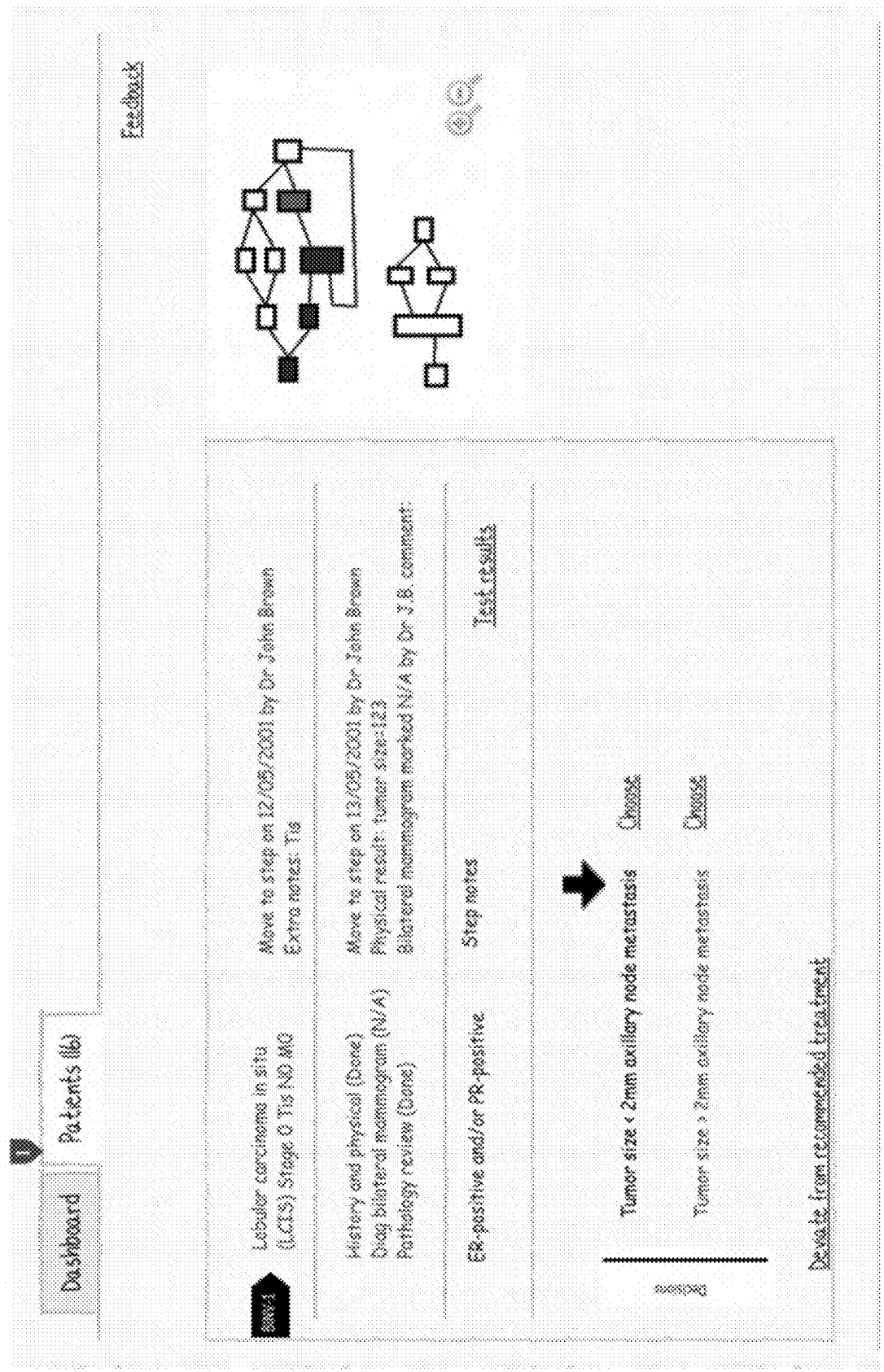
FIG. 4 shows an example of detailed information for an individual patient's medical history.

FIG. 4 shows detailed information for an individual patient's medical history. The user can view, in real time, detailed medical history information for each patient, previous test results and the next recommend treatment options along the treatment guideline or pathway. The user can scroll back to view the medical history and access individual diagnosis or test results for each individual patient. Test results may be entered directly into this screen by a user which will automatically identify and recommend the next treatment step by searching the underlying relevant treatment pathway or guideline, which has been digitized and coded into a dynamic database, which will identify the relevant next treatment step.

Figure 5:
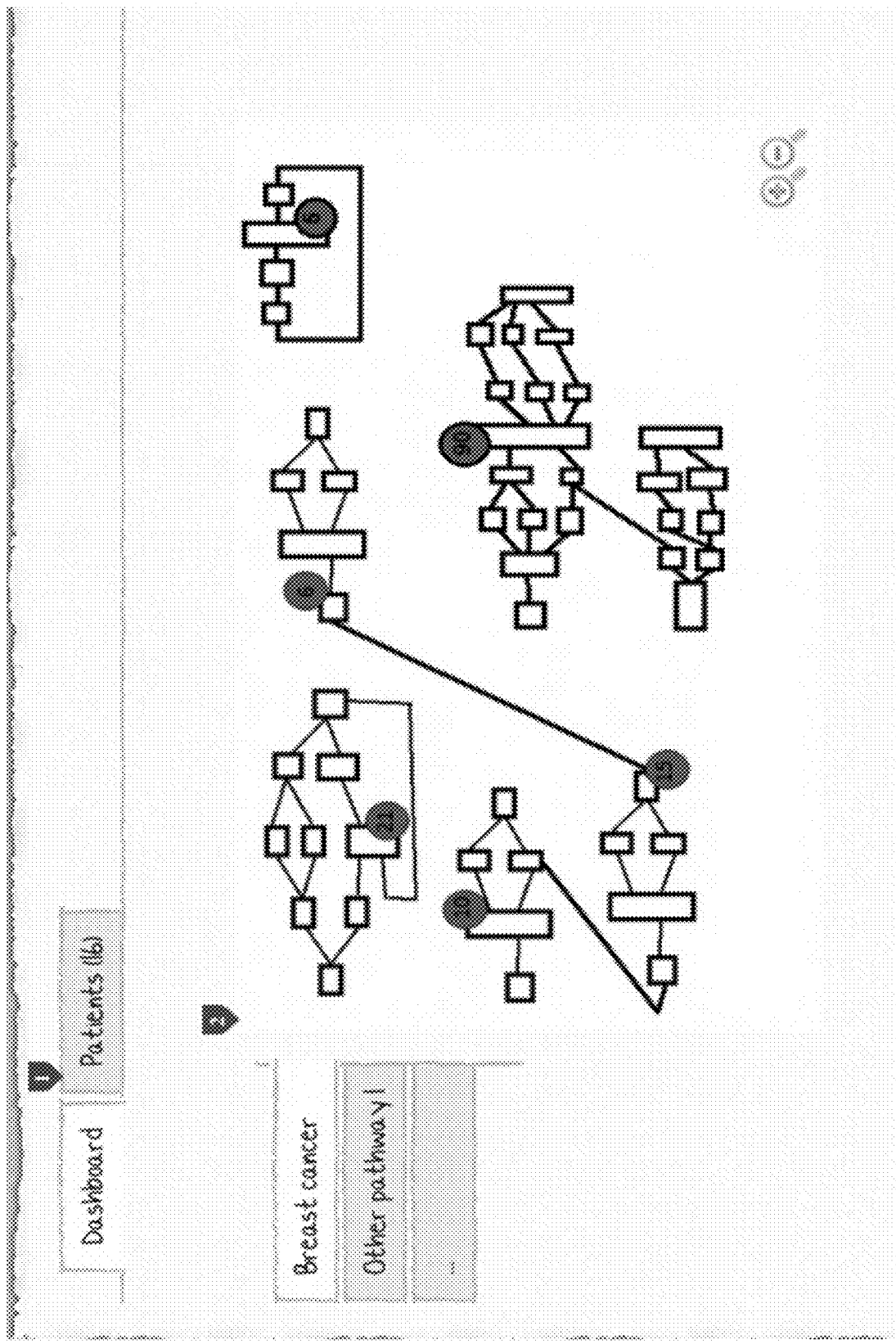
FIG. 5 shows an example of patients at points along the pathway.

FIG. 5 shows patients at points along the pathway. The process software allows users to view in real time an overview of the process, treatments, test results and other medical information in order to position patients at the correct point on the guidelines, pathway or best practice treatment stages. The ability to view all patients currently undertaking treatment at any point along the pathway can be overlaid upon the pathway is also there. The user will be able to zoom in or out to view the pathway in greater detail or for a high-level perspective. Patient's position will be maintained at the correct point on the pathway at any zoom level. Scrolling over or clicking on a group of patients will open further screens with more detailed patient information and medical history. Patients or groups of patients that are following the treatment as per the guidelines appear in green, the patients or groups of patients that are deviating from the treatment guidelines will appear in red and should a group of patients at a single node consist of both on-track and off-track with respect to treatment guidelines, the highlight report will appear in amber. This solution allows users, institutions or entities to view in real time at what treatment stage any patient under their care is currently located. This also allows the identification of over and underutilization of resources needed to carry out medical tests, treatments or procedures and to allow for effective resource allocation and planning and the supervising physicians can manage the treatment progress of multiple patients by graphically demonstrating at what stage all patients under their care are currently positioned.

Figure 6:
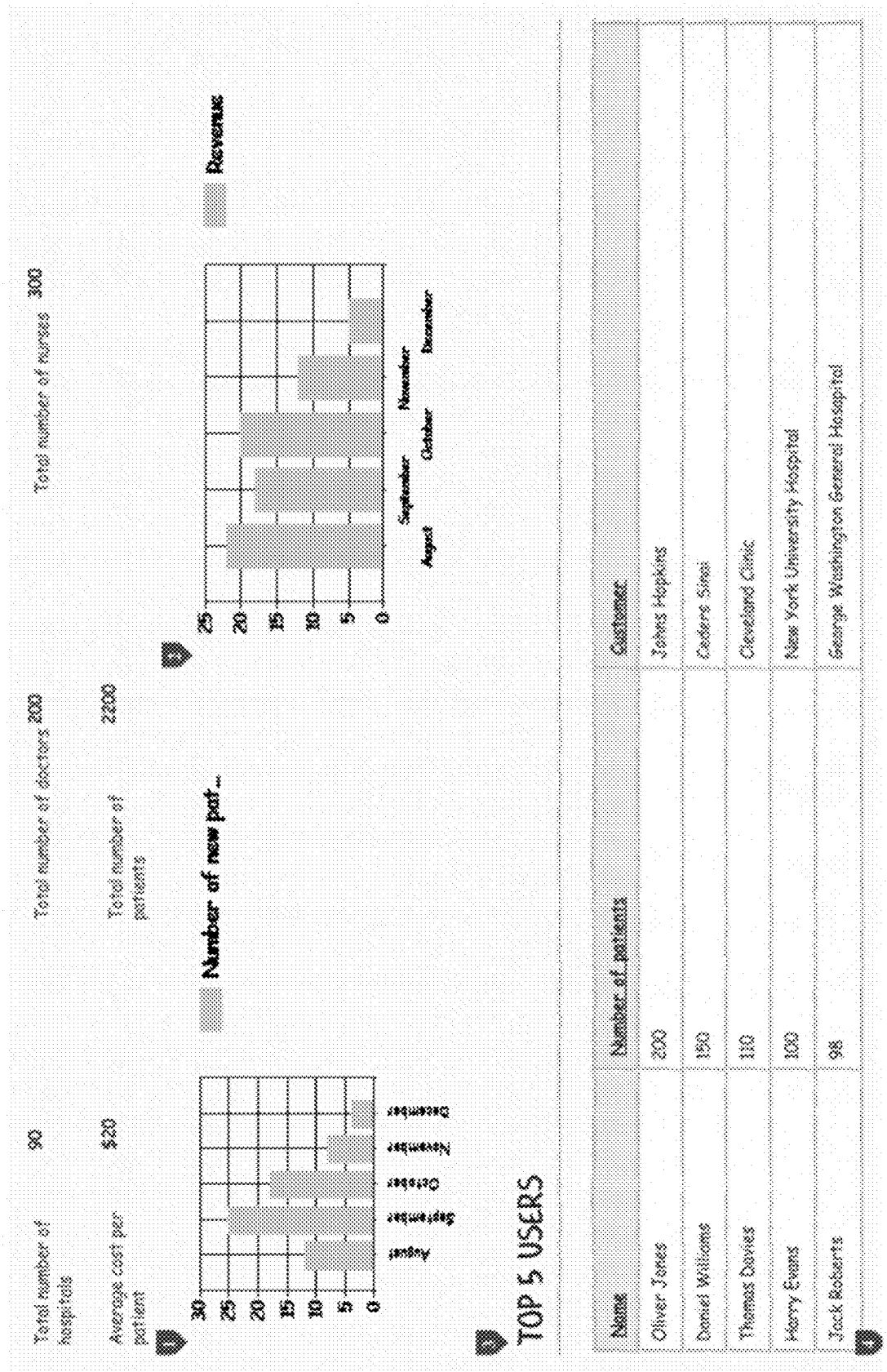
FIG. 6 shows an example of a view for tracking user and financial revenue information.

FIG. 6 shows view for tracking user and financial revenue information. Owners of this product, overall users or administrator's dashboard view for tracking user and financial revenue and expenditure information. The users (such as administrators) will be able to view in real time detailed information on revenue, users and patients. Information can be displayed in a time specific manner on a monthly, quarterly or annual basis. A management module evaluates and displays financial information and treatment information on an individualized basis or in a consolidated manner for any group of patients, users, institutions or procedures. The management module shows the total number of clients (e.g. doctors, medical institutions, other), revenue generated, expenditure, total number of patients registered on the system and in ongoing care, most active users, and other management, user, patient and financial information.

FIG. 7 shows all changes made to the system with the ability to search by date or by keyword. Here the user can search and filter the whole system with the help of keywords.

Figure 8:
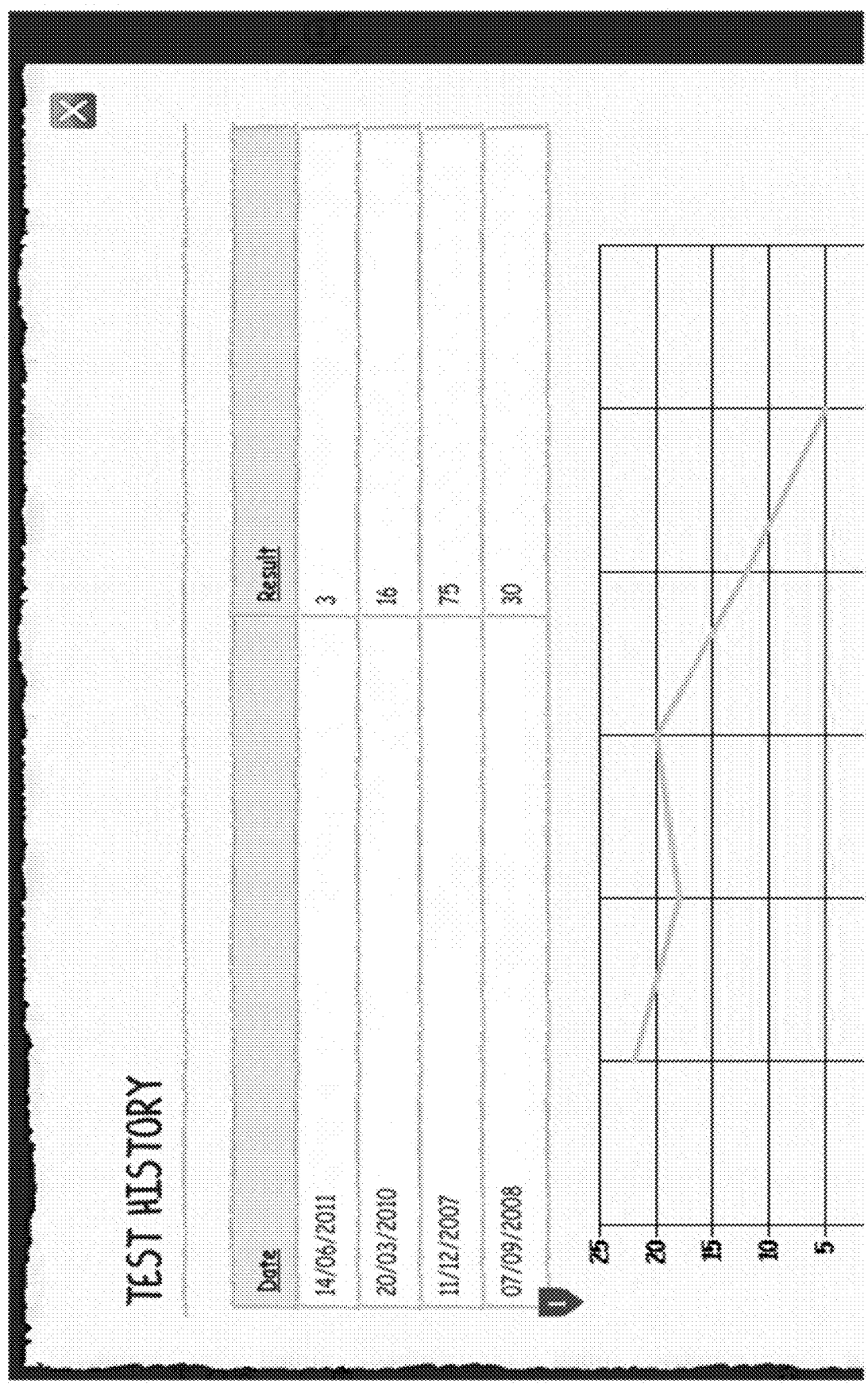
FIG. 8 shows an example of consolidated information on test results.

FIG. 8 shows consolidated information on test results. Data input from FIG. 4 and consequently FIG. 10 will be automatically updated in this screen for each individual patient. Test results for an individual patient are displayed by date and displayed in a graphical manner to assist with interpretation of the data. A consolidated view of all test results can be displayed. Test results for an individual can be forwarded to other physicians or medical institutions. The cost of a specific medical test or treatment can be associated with each test type to provide the user with a visual representation of the cost per test and ongoing cost incurred for a given patient as they progress through the specific treatment path.

FIG. 9 shows secure and confidential database of patient demographics and identifying information. Individual patient data once entered can be displayed in a consolidated manner whereby the user can select an individual patient row to edit patient information, remove a patient, transfer a patient to another institution or to delete or archive patient (removes the patient from the consolidated views but does not delete the data completely) information. Editing or changing patient information is password protected and all changes are tracked to ensure a proper audit trail is maintained. This module allows search and filter function.

Figure 10:
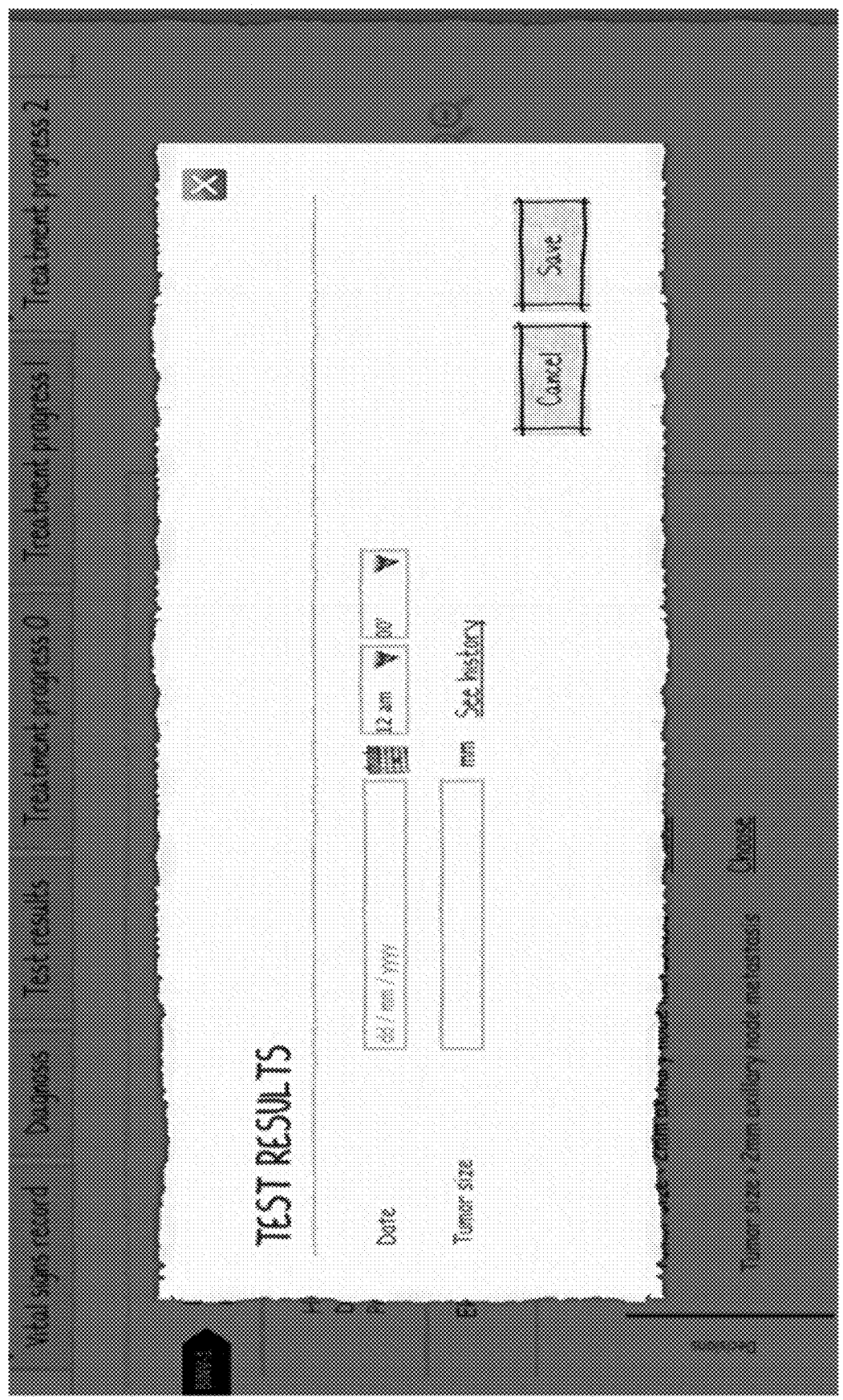
FIG. 10 shows an example of a module which allows a physician or nurse or other user to enter test results.

FIG. 10 shows a module which allows a physician or nurse or other user to enter test results. User will enter the date, time and information related to a specific test that has been carried out at the request of the supervising physician. Data entered on test results is automatically updated to the individual patient's medical history and triggers the next recommendation along the pathway based on the pre-determined criteria. The supervising physician is notified automatically of the test result that is input here and provided with the next most suitable treatment options.

Figure 11:
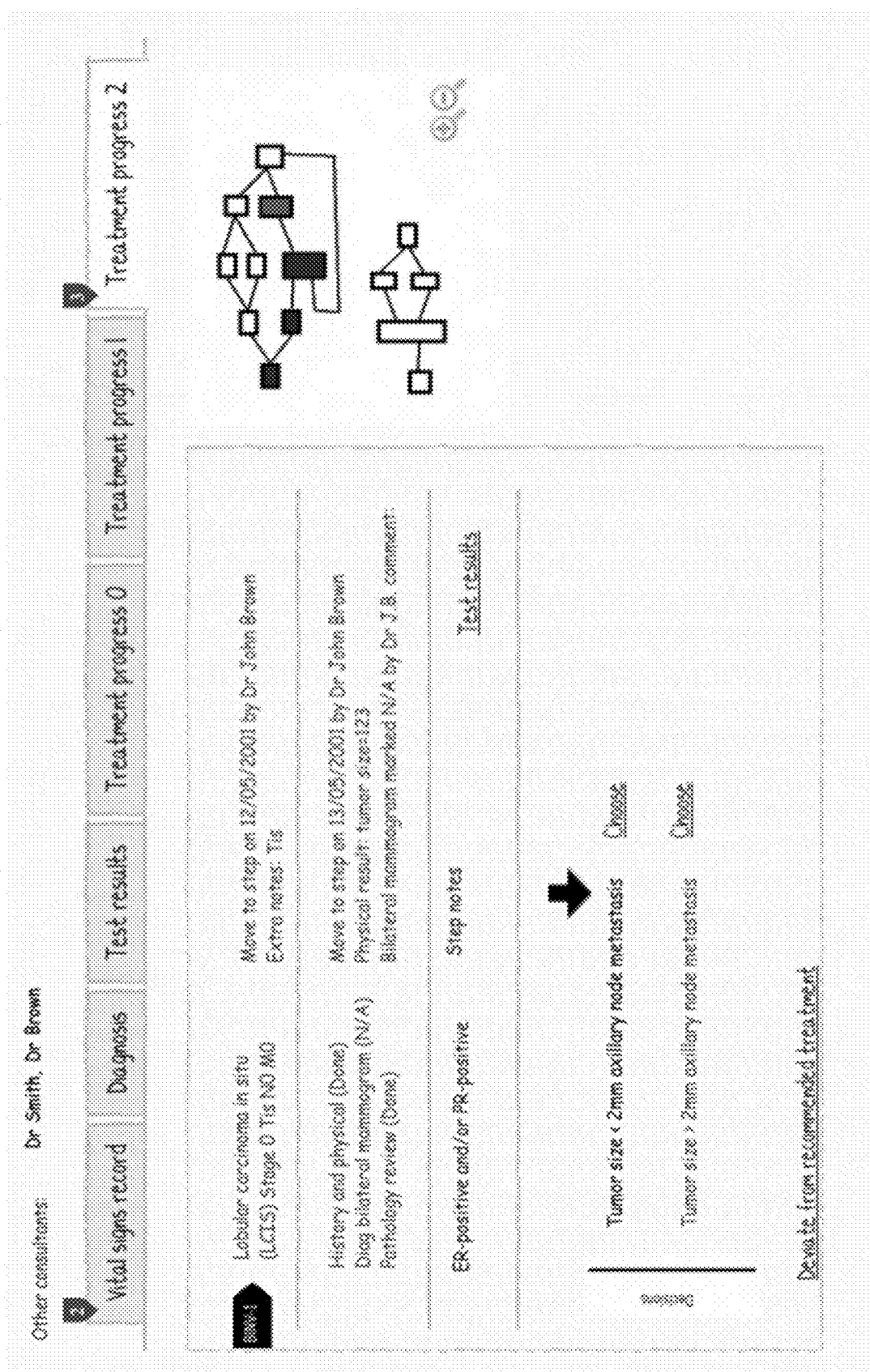
FIG. 11 shows an example of an individual patient's progress along the relevant pathway.

FIG. 11 shows an example of an individual patient's progress along the relevant pathway.

Figure 12:
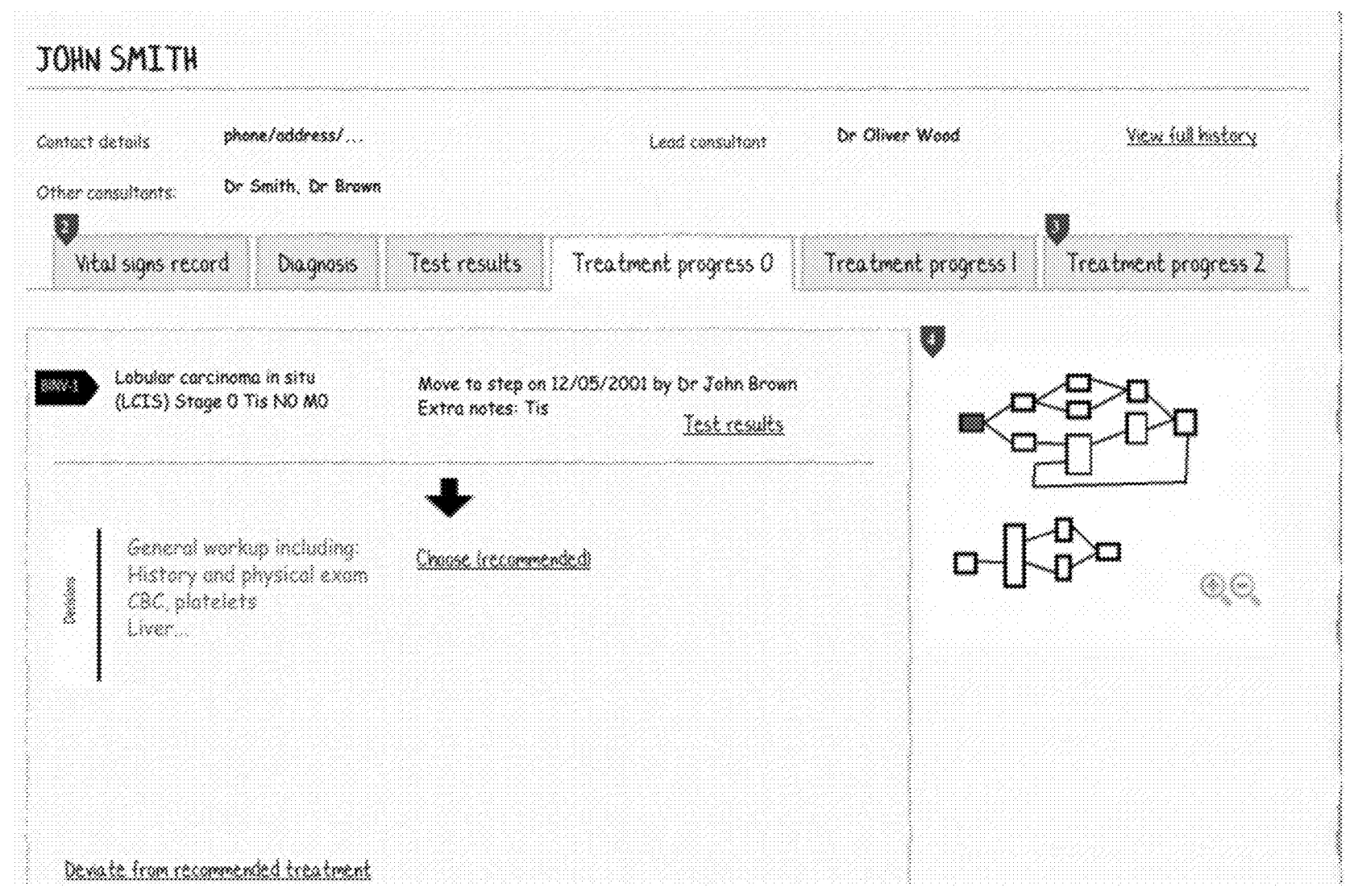

FIG. 12 shows another example of an individual patient's progress along the relevant pathway. A user may view detailed information on the current status of the patient, the position on the treatment pathway, any test results, a record of the vital signs that may have been taken in the past, the original diagnosis and the physicians that are attending this patient.

FIG. 13 shows a view of all tests that have taken place for each individual patient, the result of the test, the time and date of the test. The cost of each test can be associated with each treatment or test to provide a financial summary of the costs incurred so far each patient based on the treatment or test that has been carried out and the cost of carrying out such a test.

FIG. 14 shows the view of license tab of the owners or this product or administrators view of the license types and pricing offered to clients of the product based on this invention. Product owners will be able to view or modify the price, and terms of use for each individual client. The product owners will be able to view all clients using the system, any special terms that have been agreed with the client, the costs of the service the client has agreed to pay and the expiry period of any agreement. Owners or administrators can edit the terms of use with the necessary access rights. Client contact information is recorded to allow for automatic reminders to be sent to users prior to the expiration of any user agreement and to automatically facilitate the renewal of service.

Figure 15:
FIG. 15 shows an example of an owner's view of all users with access to the system.

FIG. 15 shows owner's view of all users with access to the system. Owners or administrators can suspend an institution or other organization or edit contact details with respect to maintenance of the user agreement (contact details etc.).

FIG. 16 shows the view of the audit trail to track changes to each patient's record. All changes to a patient's record will be logged and details of the change recorded. This will also include name of the person changing any information, time, date and description of the change. This tab also has the search/filter function.

FIG. 17 shows user maintenance, access permissions and password details. This displays users including different levels of access and rights. The ability to reset passwords for individual users is also provided along with Contact details for individual users. The ability to send mass emails to notify users of system related updates or changes along with the ability to set access rights to individual users in order to perform or restrict users from specific tasks is also there. For example users categorized as 'admin' would not be able to input test results. A search/filter function to allow for swift navigation is enabled.

FIGS. 18 and 27 show an interface to allow for editing the underlying database of guidelines or treatment best practices. This interface allows modification of guidelines or best practices based on the emergence of new information or studies, changes in the philosophy of care and availability of resources. Any changes to the underlying database are sent for ratification prior to a system wide upgrade. The user may view the proposed change to the database and may reject it or accept or propose changes. Utilizing existing user contact details any changes to the treatment guidelines or best practices in the database can be forwarded automatically to physicians.

Figure 19:
FIG. 19 shows an example of a physician's view of each patient.

FIG. 19 shows a physician's view of each patient. The physician may view for each patient a detailed summary of vital signs, diagnosis test treats and any treatment that has taken place. Multiple diagnoses can be shown with the date that each diagnosis took place.

Figure 20:
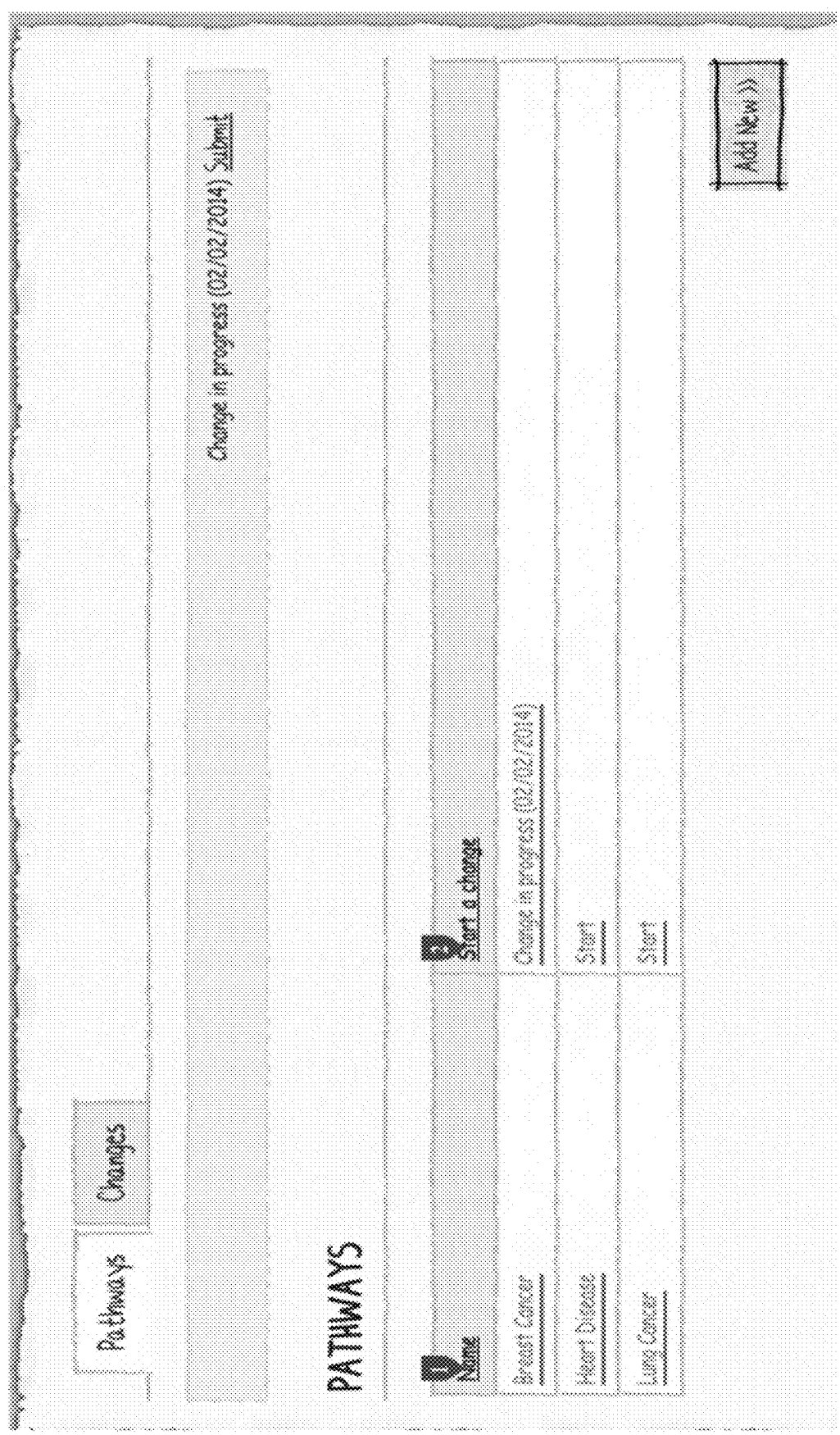
FIG. 20 shows an example of a database editing interface.

FIG. 20 shows a database editing interface to allow access to multiple pathways that may be supported on the product. A searchable database of any guidelines and/or best practices many be edited, including but not limited to guidelines and best practices published by governments, medical institutions, associations or private entities and individuals e.g. NCCN guidelines for breast cancer care.

FIG. 21 shows an individual patient details screen. A display of each patient and the institution at which treatment is taking place is there in this interface. A user may transfer a patient and all relevant patient history stored on the system to another institution.

FIG. 22 shows a display of each visit by a patient. This interface allows the user to input any vital medical information such as blood pressure, heart rate and other measures for record keeping purpose.

FIG. 23 shows Owner or administrator's view of messages sent to clients. By virtue of this function updates may be sent to multiple clients to inform about system updates, upgrade and changes. This interface also has records of all messages sent in the past.

Figure 24:
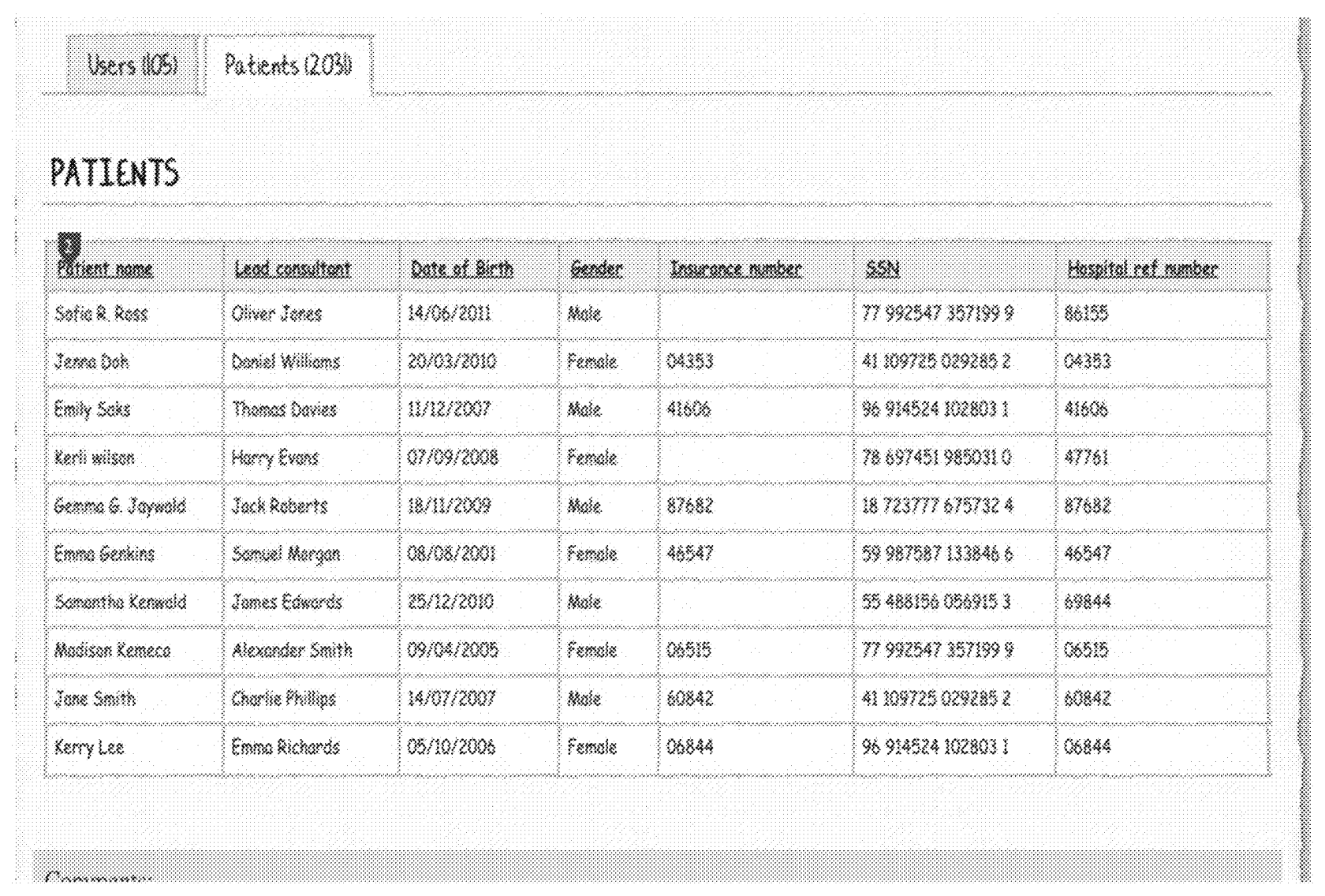

FIG. 24 shows a display of patient's insurance details and lead physician attending each patient. This interface allows hospitals, medical institutions and other organization to ensure that all patients under their care are correctly recorded with key medical staff, insurance details and other important information is recorded for billing and cost tracking and allocation purposes. A medical institution or other organization can monitor the patient under the care of each lead physician and any insurance or cost details under each physician's care.

FIG. 25 shows a display that allows support staff to be allocated to a patient, which in turn permits the entry of relevant details to each patient's record, such as blood pressure or vital signs. Once a nurse or other support staff is allocated to a patient they will be automatically notified of any pending tasks or requests scheduled in the future with respect to this patient. Hospitals, medical institutions and other organizations can monitor resource allocation to patients to ensure that over or underutilization is minimized. A consolidated view with analytical data such as ratios of number of staff to patients can be produced in real time.

Figure 26:
FIG. 26 shows an example of another consultants tab.

FIG. 26 shows a display that allows specialist physicians to be allocated to patient which in turn permits the allocated staff member to input relevant diagnostic details to each patient's record. Once a physician is allocated to a patient they will be automatically notified electronically of any pending tasks or requests scheduled in the future with respect to the patient. Hospitals, medical institutions and other organizations can monitor resource allocation to patients to ensure that over or underutilization is minimized. A consolidated view with analytical data such as ratios of number of staff to patients can be produced in real time. This allows and provides for collaboration among different medical specialists and types of providers improving coordination of patient care. This interface can monitor resource allocation to patients to ensure that overutilization or underutilization of specialists, equipment, employees and investment is minimized.

This invention may be designed as a web application accessible by internet browsers or similar platforms. The application could be either hosted on a Cloud or tradition server by a third party specialist hosting supplier like Amazon, RackSpace® or EasySpace or on any internally hosted Window Server. The instant invention will be based on SaaS (Software as a Service) architecture. This will allow a single installation of the application on a secure server while allowing different tenants (hospitals, etc.) to subscribe to the service and run autonomously of each other. Each tenant will be able to manage their own branding (how the application will look) and users (doctors) account permissions. Doctors will be able to create and manage a patient treatment case from beginning to end.

This invention may be used in non-medical discipline when best practices are to be used or where complex guidelines are to be implemented.

While specific embodiments of the present invention have been provided, it is to be understood that these embodiments are for illustration purposes and not limiting. Many additional embodiments will be apparent to persons of ordinary skill in the art reading this disclosure.

What is claimed is:

1. A computer-implemented healthcare platform for the treatment of complex disease in a healthcare provider organization, the platform comprising at least one digital data processing device comprising at least one processor capable of performing executable instructions, an operating system configured to perform data input and output, and one or more data storage memory devices, the platform further comprising:

a) a database of users comprising, for each user, a level of access and rights, the level of access and rights selected from a list comprising a healthcare provider user level of access and rights and a healthcare supervisor level of access and rights, wherein each user with a healthcare supervisor level of access and rights is associated with one or more users with a healthcare provider level of access and rights;

b) a database of patient records comprising, for each patient, identifying information, demographic markers, and medical history including test results; and c) a database of treatment guidelines, each treatment guideline comprising at least three multistep pathways, the database of treatment guidelines comprising ratified and unratified treatment guidelines;

the at least one digital processing device loaded with a computer program comprising instructions executable to create a healthcare provider user application comprising:

a) a software module providing a treatment guideline editing interface allowing a healthcare provider user to change steps, add steps, and remove steps of each pathway of each treatment guideline, view edits to treatment plans derived from the treatment guideline made by other healthcare provider users, wherein the edits made by others are flagged if non-compliant with the treatment guideline, and submit an edited treatment guideline for ratification by a healthcare supervisor user, wherein each edit comprises one or more annotations of justification details;

b) a software module dynamically mapping a patient record to a selected treatment guideline from the database of treatment guidelines to create an individualized treatment plan, the selected treatment guideline being a ratified treatment guideline or an unratified treatment guideline edited by the healthcare provider, wherein the mapping comprises i) positioning the patient on a point on a selected pathway of the selected treatment guideline, ii) recommending a next treatment step for the patient on the selected path of the selected treatment guideline, and iii) displaying a graphical overview of the patient's progress along the selected pathway of the selected treatment guideline in real-time, including the recommended next treatment step;

c) a software module providing a user interface comprising interface elements allowing the healthcare provider user to edit the individualized treatment plan by i) changing the mapping of the patient record to a different selected treatment guideline, ii) editing the positioning of the patient on the selected treatment guideline, iii) sustaining the recommended next treatment step, rejecting the recommended next treatment step in favor of an alternative next treatment step in the selected treatment guideline, or adding a next treatment step non-compliant with the selected treatment guideline; and d) a software module generating an audit trail tracking all changes to each patient's record, wherein the audit trail records edits to the individualized treatment plan that are compliant with the selected treatment guideline and flags edits that are non-compliant with the selected treatment guideline;

the at least one digital processing device further loaded with a computer program comprising instructions executable to create a healthcare supervisor user application comprising:

a) a software module allowing a healthcare supervisor user to manage the database of users, including the assignment of the levels of access and rights;

b) a software module displaying a graphical overview of each patient's progress simultaneously in the individualized treatment plan currently assigned to the patient and based on each treatment guideline in real-time for patients treated by the one or more healthcare provider users associated with the healthcare supervisor user; and c) a software module providing a user interface comprising interface elements allowing the healthcare supervisor user to view each edit to treatment guidelines made at the treatment guideline editing interface, view each annotation associated with each edit, and ratify or reject each edit to treatment guidelines, wherein ratification of an edited treatment guideline makes the edited treatment guideline available for use by healthcare provider users associated with the healthcare supervisor user.

2. The computer-implemented healthcare platform of claim 1, wherein each treatment guideline comprises at least one pathway diverging into two or more distinct pathways based on: a patient test, a patient biopsy result, a patient response to treatment, a patient tolerance of treatment, a patient symptom change, or a combination thereof.

3. The computer-implemented healthcare platform of claim 2, wherein each treatment guideline comprises at least one pathway diverging into two or more distinct pathways based on: a choice of a treatment step from among a plurality of treatment steps presented in the treatment guideline or added to the treatment guideline via the treatment guideline editing interface.

4. The computer-implemented healthcare platform of claim 1, wherein the complex disease is cancer and the selected treatment guideline is a cancer treatment guideline.

5. The computer-implemented healthcare platform of claim 4, wherein the complex disease is breast cancer and the selected treatment guideline is a breast cancer treatment guideline.

6. The computer-implemented healthcare platform of claim 1, wherein the healthcare provider user application selects the treatment guideline based at least on the patient's current condition, medical history, and test results.

7. The computer-implemented healthcare platform of claim 1, wherein the healthcare provider user application positions the patient on a point on a pathway of the selected treatment guideline based at least on the patient's current condition, medical history, and test results.

8. The computer-implemented healthcare platform of claim 1, wherein the healthcare provider user application maps the patient record to the selected treatment guideline based at least on the patient's current condition, medical history, and test results.

9. The computer-implemented healthcare platform of claim 1, wherein the healthcare provider user application recommends the next treatment step based at least on the patient's current condition, medical history, test results, and achievement of prerequisites for the treatment step.

10. The computer-implemented healthcare platform of claim 1, wherein the software module allowing the healthcare provider user to sustain the recommended next treatment step, reject the recommended next treatment step in favor of an alternative next treatment step in the selected treatment guideline, or add a next treatment step non-compliant with the selected treatment guideline further allows the healthcare provider user to input justifications for rejected or added treatment steps.

11. The computer-implemented healthcare platform of claim 1, wherein the healthcare provider user application further comprises a software module creating alerts for the healthcare provider user when a new clinical trial, new test results, or treatment results are available for the patient.

12. The computer-implemented healthcare platform of claim 1, wherein the healthcare provider user application further comprises a software module providing an interface for communication and collaboration among other healthcare provider users and healthcare supervisor users.

13. The computer-implemented healthcare platform of claim 1, wherein the healthcare supervisor user application further comprises a software module creating alerts for the healthcare supervisor user if a patient record indicates that an individualized treatment plan deviates from, or is not in compliance with, the selected treatment guideline.

14. The computer-implemented healthcare platform of claim 1, wherein the healthcare supervisor user application displays a graphical overview of each patient's progress in individualized treatment plans based on each treatment guideline that highlights patients that have deviated from the recommended treatment and shows justification for any deviations.

15. The computer-implemented healthcare platform of claim 1, wherein the healthcare supervisor user application displays a graphical overview of each patient's progress in individualized treatment plans based on each treatment guideline that identifies overutilization and underutilization of resources needed to carry out medical tests, medical treatments, and medical procedures.

16. The computer-implemented healthcare platform of claim 1, wherein the healthcare supervisor user application displays a graphical overview of each patient's progress in the patient's individualized treatment plan based on each treatment guideline that displays cost of each medical test, medical treatment, and medical procedure for each patient or on a consolidated basis for all patients.

17. The computer-implemented healthcare platform of claim 1, wherein the healthcare provider user application further comprises a software module identifying clinical trials for which each patient is eligible and providing the healthcare provider user the option to enter each patient into an identified clinical trial for which they are eligible.

18. The computer-implemented healthcare platform of claim 1, wherein ratification of edits to a treatment guideline comprises sharing the edited treatment guideline and associated annotations across the platform for consideration by other healthcare provider organizations.

\* \* \* \* \*